United States Patent [19]

Dugar et al.

[11] Patent Number: 5,124,337
[45] Date of Patent: Jun. 23, 1992

[54] N-ACYL-TETRAHYDROISOQUINOLINES AS INHIBITORS OF ACYL-COENZYME A:CHOLESTEROL ACYL TRANSFERASE

[75] Inventors: Sundeep Dugar, Parlin, N.J.; Timothy Kogan, Half Moon Bay, Calif.

[73] Assignee: Schering Corporation, Kenilworth, N.J.

[21] Appl. No.: 702,993

[22] Filed: May 20, 1991

[51] Int. Cl.$^5$ .................. A61K 31/47; C07D 217/00
[52] U.S. Cl. ........................ 514/307; 514/310; 514/241; 514/253; 514/269; 544/215; 544/333; 544/405; 546/146; 546/147
[58] Field of Search ............... 546/146, 147; 514/307, 514/310, 241, 253, 269; 544/215, 333, 405

[56] References Cited

U.S. PATENT DOCUMENTS

| | | | |
|---|---|---|---|
| 4,460,775 | 7/1984 | Portlock | 546/147 |
| 4,514,569 | 4/1985 | Hendrickson et al. | 546/144 |
| 4,555,503 | 11/1985 | Patchett | 514/19 |
| 4,634,715 | 1/1987 | Greenlee et al. | 514/423 |
| 4,729,985 | 3/1988 | Kleinman et al. | 514/17 |
| 4,743,450 | 5/1988 | Harris et al. | 514/423 |
| 4,882,339 | 11/1989 | Wasley | 546/144 |
| 4,904,300 | 2/1990 | Schneider et al. | 546/144 |

OTHER PUBLICATIONS

Stenlake et al., *Eur. J. Med. Chem.-Chim. Ther.*, 9(3), 239-242 (1974), Chemical Abstracts 82(9):57976v.

*Primary Examiner*—C. Warren Ivy
*Assistant Examiner*—James H. Turnipseed
*Attorney, Agent, or Firm*—Anita W. Magatti; Eric S. Dicker

[57] ABSTRACT

N-acyltetrahydroisoquinolines including novel compounds of the formula

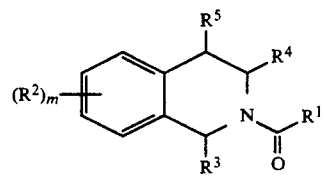

wherein
  $R^1$ is a C10–C25 alkyl chain; a substituted C10–C25 alkyl chain; an interrupted C10–C25 alkyl chain; a substituted interrupted C10–C25 alkyl chain; diphenylamino; di-($R^2$-substituted phenyl)amino; di-(heteroaryl)amino; di-$R^2$-substituted heteroary)amino; diphenylmethyl; or di-($R^2$-substituted phenyl)methyl;
  $R^2$ is hydroxy, lower alkyl, lower alkoxy, halogeno, amino, lower alkylamino or di-(lower alkyl)amino;
  $R^3$, $R^4$ and $R^5$ are independently H or —(CH$_{2n}$—Ar;
  Ar is phenyl, $R^2$-substituted phenyl, heteroaryl or $R^2$-substituted heteroaryl;
  n=0,1 or 2;
  m=0,1 or 2;

or a pharmaceutically acceptable salt thereof, useful in the treatment of atherosclerosis are disclosed.

16 Claims, No Drawings

N-ACYL-TETRAHYDROISOQUINOLINES AS INHIBITORS OF ACYL-COENZYME A:CHOLESTEROL ACYL TRANSFERASE

BACKGROUND OF THE INVENTION

The present invention relates to N-acyl-1,2,3,4-tetrahydroisoquinolines and to pharmaceutical compositions containing such compounds, for use in the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male sex, cigarette smoking and serum cholesterol. A total cholesterol level in excess of 225-250 mg/dl is associated with significant elevation of risk.

Cholesterol esters are a major component of atherosclerotic lesions and the major storage form of cholesterol in arterial wall cells. Formation of cholesterol esters is also a key step in the intestinal absorption of dietary cholesterol. The intracellular esterification of cholesterol is catalyzed by the enzyme acyl CoA:-cholesterol acyl transferase (ACAT, EC 2.3.1.26). Thus, inhibition of ACAT is likely to inhibit the progression of atherosclerotic lesion formation, decrease the accumulation of cholesterol esters in the arterial wall, and block the intestinal absorption of dietary cholesterol.

A number of N-acyl-1,2,3,4-tetrahydroisoquinoline enzyme inhibitors are known. U.S. Pat. Nos. 4,743,450, 4,634,715, 4,555,503 and European patent publication 259,838 disclose N-acyl-1,2,3,4-tetrahydroisoquinoline-3-carboxylic acid inhibitors of angiotensin I converting enzyme (ACE).

U.S. Pat. No. 4,460,775 discloses N-acyl-1,2,3,4-tetrahydroisoquinoline-1-carboxylic acid derivative ACE inhibitors.

German patent application DE 3,324,744 discloses N-acyl-1-oxo-1,2,3,4-tetrahydroisoquinoline-3-carboxylic acid ACE inhibitors.

U.S. Pat. No. 4,729,985 discloses N-acyl-1,2,3,4-tetrahydroisoquinoline renin inhibitors of the formula:

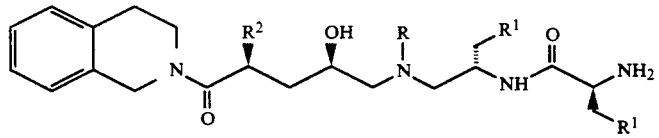

wherein R is H or methyl; $R^1$ is phenyl, 1-naphthyl, 4-hydroxyphenyl, propyl, iso-propyl, 4-imidazolyl and 4-methoxyphenyl; and $R^2$ is H, lower alkyl, lower alkoxy, phenyl or $R^3$-substituted phenyl wherein $R^3$ is ($C_1$-$C_3$)alkyl, ($C_1$-$C_3$)alkoxy, fluoro or chloro.

In addition, Chem. Abstracts 82(9): 57976v, by Stenlake, et al, discloses an N-acyl-1,2,3,4-tetrahydroisoquinoline having the structure:

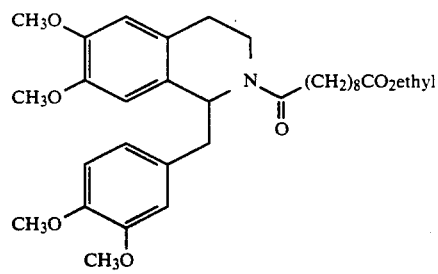

SUMMARY OF THE INVENTION

Novel compounds of the present invention are represented by the formula I

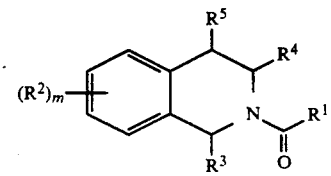

wherein
$R^1$ is an alkyl chain of 10 to 25 carbons, branched or straight, saturated or containing one or more double bonds; an alkyl chain as defined substituted by one or more substituents selected from the group consisting of di-(lower alkyl)amino and Ar; an alkyl chain as defined interrupted by one or more groups selected from the group consisting of —O—, —$SO_p$—, —NH—, —C(O)—, phenylene, $R^2$-substituted phenylene, heteroarylene and $R^2$-substituted heteroarylene, wherein p=0, 1 or 2, provided that where said alkyl chain is interrupted by one or more —NH— groups, said —NH— groups do not together with a —C(O)— group comprise an amide group; an interrupted alkyl chain as defined substituted by one or more di-(lower alkyl)amino or Ar groups; diphenylamino; di-($R^2$-substituted phenyl)amino; di-(heteroaryl)amino; di-($R^2$-substituted heteroaryl)amino; di-phenylmethyl; or di-($R^2$-substituted phenyl)methyl;

$R^2$ is independently selected from the group consisting of hydroxy, lower alkyl, lower alkoxy, halogeno, amino, lower alkylamino and di-(lower alkyl)amino;

$R^3$, $R^4$ and $R^5$ are independently H or —$(CH_2)_n$—Ar;

Ar is selected from the group consisting of phenyl, $R^2$-substituted phenyl, heteroaryl and $R^2$-substituted heteroaryl;

n=0,1 or 2;

m=0, 1 or 2;

or a pharmaceutically acceptable salt thereof.

Preferred are compounds of formula I wherein $R^1$ is $CH_3(CH_2)_7CH=CH(CH_2)_7-$ (i.e. $-C(O)-R^1$ is oleoyl), diphenylacetyl, or diphenylamino.

Also preferred are compounds of formula I wherein $R^3$, $R^4$ and $R^5$ are independently H or $-(CH_2)_n-Ar$, wherein Ar is phenyl or $R^2$-substituted phenyl.

Another group of preferred compounds is that wherein one of $R^3$, $R^4$ or $R^5$ is $-(CH_2)_n-Ar$, wherein Ar is phenyl or $R^2$-substituted phenyl, and the others are H.

More preferred are compounds of formula I wherein $R^5$ is H or phenyl, and $R^1$ is $CH_3(CH_2)_7CH=CH(CH_2)_7-$ (i.e. $-C(O)-R^1$ is oleoyl), diphenylmethyl, or diphenylamino.

Another group of more preferred compounds is that wherein $R^4$ is H, phenyl or di-(lower alkoxy)phenyl, and $R^1$ is $CH_3(CH_2)_7CH=CH(CH_2)_7-$ (i.e. $-C(O)-R^1$ is oleoyl), diphenylmethyl, or diphenylamino.

Yet another group of more preferred compounds is that wherein $R^3$ is selected from the group consisting of H, 2-(4-chlorophenyl)ethyl, 3,4-dimethoxyphenylmethyl, benzyl or 2-methylamino-5-chloro-phenyl and $R^1$ is $CH_3(CH_2)_7CH=CH-(CH_2)_7-$ (i.e. $-C(O)-R^1$ is oleoyl), diphenylmethyl, or diphenylamino.

Most preferred are compounds of formula I wherein $R^5$ is H or phenyl, $R^4$ is H, phenyl or di-(lower alkoxy)phenyl, $R^3$ is selected from the group consisting of H, 2-(4-chlorophenyl)ethyl, 3,4-dimethoxyphenylmethyl, benzyl or 2-methylamino-5-chloro-phenyl and $R^1$ is $CH_3(CH_2)_7CH=CH-(CH_2)_7-$ (i.e. $-C(O)-R^1$ is oleoyl).

This invention also relates to pharmaceutical compositions comprising an ACAT inhibitor of formula I in a pharmaceutically acceptable carrier.

In another aspect, the invention relates to the use as ACAT inhibitors of compounds of the formula Ia

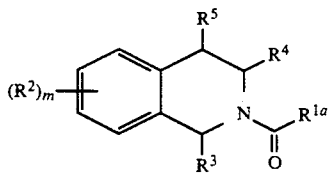

wherein
$R^{1a}$ is an alkyl chain of 1 to 25 carbons, branched or straight, saturated or containing one or more double bonds; an alkyl chain as defined substituted by one or more substituents selected from the group U; an alkyl chain as defined interrupted by one or more groups selected from the group consisting of $-O-$, $-SO_p-$, $-NH-$, $-C(O)-$, phenylene, $R^2$-substituted phenylene, heteroarylene and $R^2$-substituted heteroarylene, wherein p=0, 1 or 2; an interrupted alkyl chain as defined substituted by one or more substituents selected from the group U;

$R^2$ is independently selected from the group consisting of hydroxy, lower alkyl, lower alkoxy, halogeno, amino, lower alkylamino and di-(lower alkyl)amino;

$R^3$, $R^4$ and $R^5$ are independently H or $-(CH_2)_n-Ar$;

Ar is selected from the group consisting of phenyl, $R^2$-substituted phenyl, heteroaryl and $R^2$-substituted heteroaryl;

U is selected from the group consisting of di-(lower alkyl)amino, diphenylamino, di-($R^2$-substituted phenyl)amino, diheteroarylamino, di-($R^2$-substituted heteroaryl)amino and Ar;

n=0,1 or 2;
m=0, 1 or 2;
or a pharmaceutically acceptable salt thereof.

Compounds of formula Ia are preferably administered in a pharmaceutically acceptable carrier for use as hypolipidemic and hypocholesterolemic agents in mammals.

DETAILED DESCRIPTION

As used herein, the term "lower alkyl" means straight or branched alkyl chains of 1 to 6 carbon atoms and "lower alkoxy" similarly refers to alkoxy groups having 1 to 6 carbon atoms.

Halogeno refers to fluorine, chlorine, bromine or iodine radicals.

"Phenylene" means a bivalent phenyl group, including ortho, meta and para-substitution and "heteroarylene" similarly means a bivalent heteroaryl group.

Heteroaryl means an aromatic group having 5 or 6 ring members wherein 1-3 ring members are independently selected from the group consisting of nitrogen, oxygen and sulfur. Examples of heteroaryl groups are pyridyl, pyrimidinyl, pyrazinyl, triazinyl, pyrrolyl, furanyl and thienyl.

Where the tetrahydroisoquinolyl moiety is substituted by more than one $R^2$ group (i.e. m=2), the $R^2$ groups are the same or different and can be situated at positions 5,6,7, or 8 of the ring system.

The alkyl chain as defined in $R^1$ and $R^{1a}$ can be a radical of a synthetic or natural fatty acid, either saturated or containing one or more carbon to carbon double bonds, or can be an interrupted alkyl chain wherein one or more of the carbon atoms in the chain can be replaced by an $-O-$, $-S-$, $-SO-$, $-SO_2-$, $-C(O)-$, $-NH-$, phenylene, $R^2$-substituted phenylene, heteroarylene or $R^2$-substituted heteroarylene group. When substituted by di-substituted amino, or optionally substituted phenyl or heteroaryl groups, the alkyl chain or interrupted alkyl chain may be independently substituted on different carbon atoms, di-substituted on one carbon atom, or both.

Where an interrupted alkyl chain as defined in $R^1$ and $R^{1a}$ contains one or more groups $-NH-$, said $-NH-$ groups cannot be directly bonded to a $-C(O)-$ group such that they together comprise an amide group. Where two or more of such interrupting $-NH-$ groups are present, two of said $-NH-$ groups can be directly bonded to the same $-C(O)-$ group such that together they comprise a urea group.

One skilled in the art will recognize that the number of double bonds present, the replacement of carbon atoms in the chain and the presence of substituents on the carbon atoms in the chain are all dependent on the length of the chain: shorter alkyl chains cannot accommodate as many bonds, carbon replacements or substituents as longer alkyl chains. In general, unsaturated alkyl chains contain 1 to 4 double bonds, conjugated or non-conjugated. Typically, where carbon atoms are replaced, 1 to 4 replacement groups can be present. Similarly, when carbon atoms in the chain are substituted, 1 to 4 substituents can be present.

Examples of alkyl chains are as follows, wherein the group $-C(O)R^1$ is named: palmitoyl, stearoyl and 2,2-dimethyldodecanoyl.

Examples of unsaturated —C(O)R¹ groups are oleoyl, linoleoyl, linolenoyl, elaidoyl, eicosatetraenoyl, eicosapentaenoyl and arachidonoyl.

Examples of —C(O)R¹ groups wherein carbon atoms in the chain are replaced are: 3-methoxyl-4-(tetradecyloxy)-benzoyl, 11-[N-(2,2-diphenylacetyl)amino]undecanoyl and phenoxyundecanoyl.

An example of a di-substituted amino —C(O)R¹ group is N,N-diphenylaminocarbonyl.

Compounds of the formula I are a subclass of compounds of the formula Ia, in that compounds of formula Ia encompass all compounds of formula I as well as another class of compounds defined by the embodiments of the group R$^{1a}$. The definition of the group R$^{1a}$ includes C1 to C9 alkyl chains, substituted alkyl chains, interrupted alkyl chains and substituted interrupted alkyl chains in addition to the C10 to C25 chains defined by R¹.

Compounds of the invention may have one or more asymmetrical carbon atoms and therefore include rotational isomers. The invention includes all possible stereoisomers in both pure form and in admixture, including racemic mixtures. Isomers can be prepared using conventional techniques, either by reacting enantiomeric starting materials or by separating isomers of a compound of formula I.

Isomers may include geometric isomers, e.g. when R¹ contains a double bond. All such isomers are contemplated for this invention.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a phenol or carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared under standard reaction conditions well known in the art. For example, a carboxylic acid of formula II can be converted to the acid chloride by treatment with thionyl or oxalyl chloride in a solvent such as dichloromethane, then reacted with an amine of formula III in the presence of a tertiary amine base such as triethylamine, 4-dimethylaminopyridine (DMAP) or N-methylmorpholine (NMM):

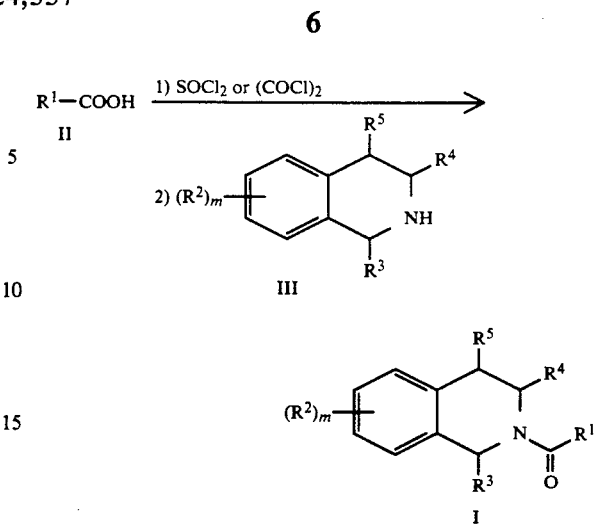

Alternatively, a salt of an amine of formula III can be similarly treated to produce a compound of formula I.

Another method involves reacting an acid of formula II and an amine of formula III in the presence of a coupling agent such as dicyclohexylcarbodiimide (DCC) or 1-(3'-dimethylaminopropyl)-3-ethylcarbodiimide (EDCI) and a base such as triethylamine, dimethylaminopyridine (DMAP) or N-methylmorpholine (NMM) in a solvent such as dichloromethane, tetrahydrofuran or dimethylformamide.

In a fourth method, the carboxy group of acid II can be activated via an active ester intermediate such as that derived from 1-hydroxybenzotriazole (HOBT).

Starting acids of formula II are commercially available or can be prepared by well known methods. Amines of formula III are either commercially available or can be prepared by various methods, several of which follow.

In a method for preparing an amine of formula IIIa, wherein R⁴ is —Ar and R³ is H, a carboxylic acid of formula IV is converted to the acid chloride V using either thionyl chloride or oxalyl chloride. The acid chloride is condensed with an aromatic compound Ar-H (VI) to give a ketone of formula VII. The ketone is reacted with hydroxylamine hydrochloride to form the oxime VIII. The oxime VIII is hydrogenated at 40-50 psi in the presence of a suitable catalyst such as 10% palladium on carbon to give an amine IX. Reaction of the amine IX with formaldehyde in methanol followed by treatment with an acid such as hydrochloric acid forms the amine of formula IIIa:

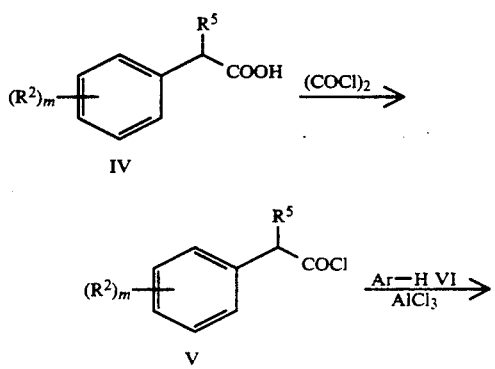

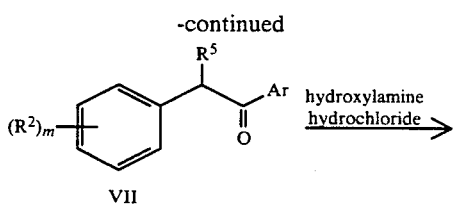

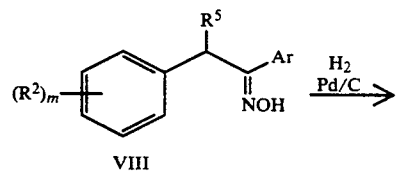

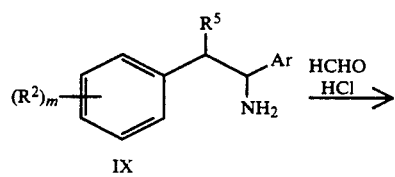

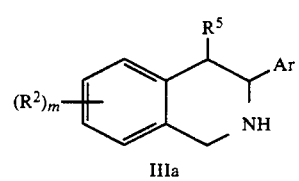

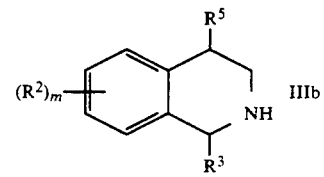

Starting amines of formula XI and aldehydes of formula X are either available from commercial sources or readily prepared by well known methods.

Another method for preparing an amine of formula IIIb consists of coupling an acid of formula XIV with an amine of formula XI to form an amide XV. The amide is treated with phosphorous oxychloride to produce an imine XVI which is reduced with sodium borohydride to the amine IIIb:

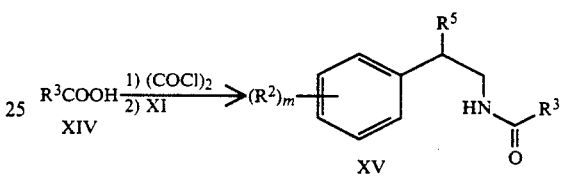

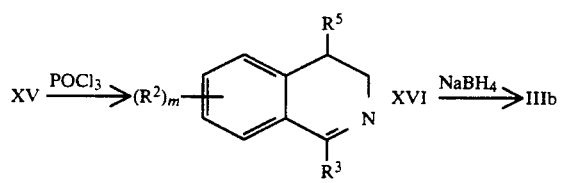

Starting acids of formula XIV are commercially available or readily prepared via known methods.

In a third method for preparing an amine of formula IIIb, an amine of formula XVII is reacted with an epoxide of formula XVIII. The resulting amino-alcohol XIX is treated with methanesulfonic acid to give the desired amine III:

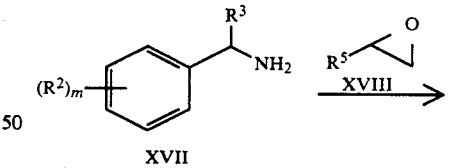

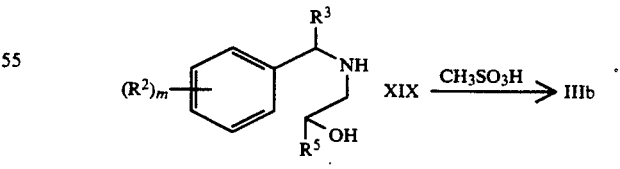

Starting amines XVII and epoxides XVIII are commercially available or can be prepared by methods well known to those skilled in the art.

Reactive groups not involved in the above processes can be protected during the reactions with conventional protecting groups which can be removed by standard procedures after the reaction. The following table shows some typical protecting groups:

Starting acids of formula IV and aryl compounds of formula VI are either commercially available or readily prepared by procedures well known to those skilled in the art.

In a method of preparing amines of formula IIIb, wherein $R^4$ is H, an amine of formula XI is condensed with an aldehyde of formula X to give an imine of formula XII. The imine is treated with an acid chloride such as 2-chloroacetyl chloride in the presence of aluminum chloride to form the cyclic amide XIII. Hydrolysis of the amide XIII using thiourea in ethanol gives the desired amine IIIb:

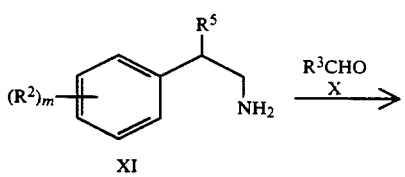

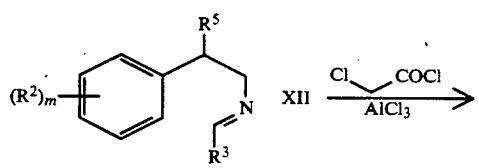

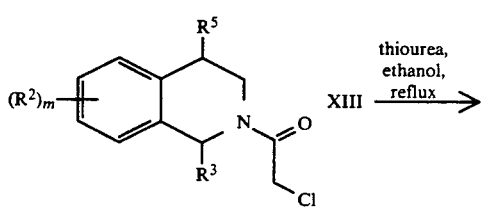

| Group to be protected | Protected group |
| --- | --- |
| —OH | —OCH₃, —OCH₂phenyl, —OSi(CH₃)₂tBu |
| —NH₂ | 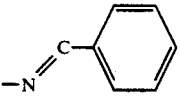, —NHC(O)OtBu |
| —COOH | —COOalkyl, —COObenzyl, —COOphenyl |

Compounds of formula Ia can be prepared by similar methods.

We have found that the compounds of formulae I and Ia are inhibitors of ACAT in vitro, novel compounds of formula I constituting a subclass of compounds of formula Ia. Thus, compounds of this invention are hypocholesterolemic and hypolipidemic agents by virtue of their ability to inhibit the esterification and intestinal absorption of cholesterol; they are therefore useful in the treatment and prevention of atherosclerosis in mammals, in particular in humans.

In addition to the compound aspect, the present invention therefore also relates to a method of treating atherosclerosis, in particular by reducing serum cholesterol, which method comprises administering to a mammal in need of such treatment a hypocholesterolemic effective amount of a compound of the formula I or Ia, or a pharmaceutically acceptable salt thereof. The compound is preferably administered in a pharmaceutically acceptable carrier suitable for oral administration.

The in vitro activity of compounds of formula I or Ia can be determined by the following procedure.

ACAT Assay (in vitro)

This assay measures the activity of ACAT by measuring the ACAT-mediated transfer of tritiated oleic acid from acyl-CoA to cholesterol to give labelled cholesterol oleate. Rat liver microsomes are used as the source of ACAT. Assays are performed in round bottom microtiterplates using a total incubation volume of 50 μL. Each incubation well receives 10 μL assay buffer (0.5M KHPO₄, 10 μM dithiothreitol, pH 7.4), 7.5 μL of 40 mg/mL BSA (Bovine Serum Albumin) and 12.5 μg of microsomal protein. The test compound (in sufficient amount to bring the final concentration to from 0.1 to 25 μM), reference compound, or vehicle control is added and the final volume brought to 47 μL. The microtiterplate is then floated on the surface of a 37° C. water bath for fifteen minutes. Incubations are started by the addition of 3 μL ³H-acyl CoA (1μCi/well, final concentration of 10 μM acyl CoA). The plate is then returned to the water bath for 15 minutes. The incubations are then terminated by application of 15 μL from each incubation to individual lanes on a thin layer plate (Silica Gel GF 20×20 cm). Standards are applied to several lanes so that the cholesterol ester band can be identified. After drying, the plates are eluted with 90:10:1 petroleum ether:diethyl ether:acetic acid. The standards are visualized via iodine vapor, and the regions corresponding to cholesterol ester are scraped into 7 mL scintillation vials. 4 mL of scintillant are added to each vial, and the radioactivity quantified. Background count is determined by the boiled controls. Full activity is determined by activity in the presence of vehicle. The percent inhibition is calculated by subtracting the background from both control and test samples, and the test value is calculated as a percentage of the control. For IC₅₀ determinations, the inhibition is plotted against drug doses on a log scale and the concentration at which 50% inhibition is obtained is determined.

Representative results are as follows:

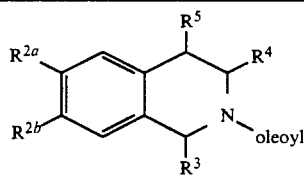

| | | | | | ACAT Inhibition Screen | | |
| --- | --- | --- | --- | --- | --- | --- | --- |
| R³ | R⁴ | R⁵ | R²ᵃ | R²ᵇ | IC50 (μM) | % Inhibition | Dose (μM) |
| H | H | H | H | H | 12 | 83 | 100 |
| H | H | H | CH₃O | CH₃O | 0.74 | 100 | 25 |
| 2-(4-chloro-phenyl)ethyl | H | H | CH₃ | CH₃O | — | 4 | 25 |
| 3,4-dimethoxy-phenylmethyl | H | H | CH₃O | CH₃O | 2.7 | 91 | 25 |
| H | H | C₆H₅ | CH₃O | CH₃O | 2.4 | 83 | 25 |
| C₆H₅—CH₂— | H | H | OH | OH | — | 73 | 25 |
| C₆H₅—CH₂— | H | H | CH₃O | CH₃O | — | 63 | 25 |
| C₆H₅—CH₂— | H | H | H | H | 4.8 | 81 | 25 |
| H | C₆H₅ | H | CH₃O | CH₃O | 3.8 | 86 | 25 |
| H | 3,4-dimethoxy-phenyl | H | CH₃O | CH₃O | — | 67 | 25 |
| 3-chloro-5-methyl-aminophenyl | H | H | H | H | — | 10 | 10 |
| C₆H₅-(cis) | H | H | CH₃O | CH₃O | — | 66 | 10 |
| C₆H₅-(trans) | H | H | CH₃O | CH₃O | 8 | 87 | 10 |

Following are preparations of starting materials and examples of preparing compounds of formula I.

PREPARATION 1

6,7-dimethoxy-3-phenyl-1,2,3,4-tetrahydroisoquinoline

Step A: Combine 3.9 g of oxalyl chloride, 2.0 g of 3,4-dimethoxyphenylacetic acid and 50 mL of benzene and stir the mixture at 60° C. for 2.5 h. Remove the excess oxalyl chloride by distillation and concentrate the solution to a volume of 20 mL. Cool the solution to room temperature and add slowly to a suspension of anhydrous aluminium chloride (1.6 g) in 300 mL of benzene over 12 h. Stir the reaction mixture for 6 h., pour into a mixture of ice and conc. hydrochloric acid, then extract with ethyl acetate. Dry the organic extract over Na$_2$SO$_4$, filter and concentrate the filtrate to a residue. Chromatograph the residue on silica gel using 3:7 ethyl acetate/hexane to give 847 mg of α-(3,4-dimethoxyphenyl)-acetophenone. $^1$H NMR (CDCl$_3$): δ8.1–7.98 (2H, m); 7.62–7.4 (3H, m); 6.76–6.9 (3H, m); 4.24 (2H, s); 3.85 (6H, s).

Step B: Add 250 mg of hydroxylamine hydrochloride to a solution of the ketone from step A in 10 mL of pyridine at 0° C. and stir for 3.5 h. Pour the reaction mixture into water and extract with diethyl ether. Wash the ethereal extract with water and 1N HCl (aqueous), then dry over Na$_2$SO$_4$. Filter and concentrate the filtrate to a residue. Chromatograph the residue (silica gel, 1:1 ethyl acetate/hexane) to give 853 mg of the desired oxime. $^1$H NMR (CDCl$_3$): δ7.67–7.55 (2H, m); 7.4–7.27 (3H, m); 6.86–6.64 (3H, m); 4.16 (2H, s); 3.8 (3H, s); 3.78 (3H, s).

Step C: Dissolve the oxime from step B in a solution of 1M HCl in ethanol (20 mL) and hydrogenate at 48 psi over 10% palladium on carbon (25 mg) for 3 h. Filter the mixture, neutralize the filtrate with NaHCO$_3$ (aqueous) and extract with ethyl acetate. Concentrate the organic extract to give 275 mg of 1-phenyl-2-(3,4-dimethoxyphenyl)ethylamine. $^1$H NMR (CDCl$_3$): δ7.42–7.2 (5H, m); 6.84–6.68 (2H, m); 6.57 (1H, d, J=2 Hz); 4.17 (1H, dd, J=9 and 5 Hz); 3.86 (3H, s); 3.78 (3H, s); 2.97 (1H, dd, J=14 and 5 Hz); 2.78 (1H, dd, J=14 and 9 Hz); 1.57 (2H, br. s).

Step D: Heat a mixture of the amine from step C, 36% formaldehyde (1 mL) and 1.5 mL of methanol at reflux for 2 h. Distill off the solvent, add 3 mL of benzene to the residue and concentrate in vacuo to a residue. Add 3 mL of benzene and again concentrate to a residue. Add 2 mL of methanolic HCl (1.5N) and heat the mixture at reflux for 2 h. Pour the mixture into water, neutralize with NH$_4$OH and extract with ethyl acetate. Concentrate the extract to give 286 mg of the title compound. $^1$H NMR (CDCl$_3$): δ7.53–7.23 (5H, m); 6.6 (2H, d, J=2 Hz); 4.3–3.72 (3H, m); 3.87 (3H, s); 3.85 (3H, s); 2.9 (2H, d, J=7 Hz).

Using a similar procedure 3-(3,4-dimethoxyphenyl)-6,7-dimethoxy-1,2,3,4-tetrahydroisoquinoline can be prepared.

PREPARATION 2

6,7-dimethoxy-1-phenyl-1,2,3,4-tetrahydroisoquinoline

Step A: Heat a solution of 2-(3,4-dimethoxyphenyl)ethylamine (1 g) and benzaldehyde (585 mg) in toluene (25 mL) at reflux for 3 h. Distill off the solvent to give N-[2-(3,4-dimethoxyphenyl)ethyl]benzylimine (1.5 g). $^1$H NMR (CDCl$_3$): δ8.14 (1H, s); 7.74–7.66 (2H, m); 7.46–7.36 (3H, m); 6.82–6.72 (3H, m); 3.85 (3H, s); 3.84 (2H, t, J=7 Hz); 3.79 (3H, s); 2.98 (2H, t, J=7 Hz).

Step B: Dissolve 200 mg of the imine from step A in 1,2-dichloroethane (8 mL), add 84 mg of 2-chloroacetylchloride and stir the mixture for 15 minutes. Add 100 mg of aluminum chloride (anhydrous) and stir for 3 h. Pour the reaction mixture into conc. HCl and ice, then extract with chloroform. Wash the chloroform extract successively with water, NaHCO$_3$ (aqueous) and brine, then concentrate to give 200 mg of N-(2-chloroacetyl)-6,7-dimethoxy-1-phenyl-1,2,3,4-tetrahydroisoquinoline.

Step C: Heat a mixture of thiourea (45 mg), the product of step B and ethanol (8 mL) at reflux for 3 h. Remove the solvent in vacuo, dissolve the residue in chloroform and filter. Concentrate the filtrate to give 153 mg of the title compound. $^1$H NMR (CDCl$_3$): δ7.4–7.18 (5H, m); 6.63 (1H, s); 6.24 (1H, s); 5.03 (1H, s); 3.85 (3H, s); 3.61 (3H, s); 3.28–2.65 (4H, m); 2.3 (1H, br. s).

PREPARATION 3

1-[2-(4-chlorophenyl)ethyl]-6-methyl-7-methoxy-1,2,3,4-tetrahydroisoquinoline

Step A: Heat a solution of 2-(3-methyl-4-methoxyphenyl)ethylamine (64.4 g) and 3-(4-chlorophenyl)-propionic acid (70.2 g) in xylene (600 mL) at reflux over a Dean-Stark trap for 5.5 h. Pour the hot reaction mixture into water an allow to stand overnight. Filter to collect the solid and recrystallize from ethanol to give N-[2-(3-methyl-4-methoxyphenyl)ethyl]-3-(4-chlorophenyl)-propionamide (101.1 g), mp=142°–144° C.

Step B: Heat a mixture of the amide from step A (10.0 g), phosphorous pentoxide (25 g), phosphorous oxychloride (15 mL) and xylene (250 mL) at reflux for 2 h. Cool the reaction mixture, slowly add water (500 mL), basify using NaOH and extract with benzene. Concentrate the benzene extract to a residue and triturate with diethyl ether to give 6-methyl-7-methoxy-1-[2-(4-chlorophenyl)ethyl]-3,4-dihydroisoquinoline (4.95 g), mp=122°–124° C.

Step C: Add sodium borohydride (2.0 g) to a suspension of the dihydroisoquinoline from step B (4.75 g) in ethanol (175 mL) and stir the mixture for 2 h. Concentrate to a residue, treat with water and heat on a steam bath for 0.75 h. Cool the mixture to room temperature, extract with ether and concentrate the ethereal extract to a residue. Dissolve the residue in ethyl acetate, treat with 1.7 g of maleic acid and recrystallize the resulting salt from ethanol/ethyl acetate to give the title compound as the maleate salt (4.05 g). Elemental analysis: calc. for C$_{19}$H$_{22}$ClNO$_2$, C=63.9%, H=6.03%, N=3.25%; found, C=63.91, H=5.99, N=3.22.

Using a similar procedure, 1-benzyl-6,7-dimethoxy-1,2,3,4-tetrahydroisoquinoline can be prepared.

PREPARATION 4

6,7-dimethoxy-4-phenyl-1,2,3,4-tetrahydroisoquinoline

Step A: Heat a solution of 3,4-dimethoxybenzylamine (16.7 g) and styrene oxide (12.0 g) in acetonitrile (250 mL) at reflux for 16 h. Concentrate to a residue and distill the residue, collecting the fraction distilling above 120° C. (0.5 mm). Recrystallize the solidified distillate from benzene/hexane to give N-(3,4-dimethoxybenzyl)-2-hydroxy-2-phenylethylamine (13.4 g), mp=93°–94° C.

Step B: Add the amino-alcohol from step A (2.2 g) to a mixture of methanesulfonic acid (100 mL) and dichloromethane (150 mL) and stir overnight at room temperature. Pour the mixture into ice-water, separate and concentrate the organic layer to a residue. Triturate with benzene then recrystallize from ethanol to give 8.7 g of the title amine as the methanesulfonate salt, mp=198°–199° C.

PREPARATION 5

1-benzyl-6,7-dihydroxy-1,2,3,4-tetrahydroisoquinoline:

Treat 1-benzyl-6,7-dimethoxy-1,2,3,4-tetrahydroisoquinoline (10 g) with 48% HBr (100 mL) and heat the mixture at reflux under nitrogen for 2 h. Cool the mixture to room temperature and allow crystals to form overnight. Collect the crystals and wash with cold ethanol to give 7.5 g of the title compound as its HBr salt, mp=233°-236° C.

EXAMPLE 1

N-(6,7-dimethoxy-1-phenyl-1,2,3,4-tetrahydroisoquinoline)-9-Z-octadecenamide

Add 188 mg of oleoyl chloride to a solution of 6,7-dimethoxy-1-phenyl-1,2,3,4-tetrahydroisoquinoline (153 mg) and triethylamine (76 mg) in dichloromethane (5 mL) and stir for 2 h. Pour the mixture into water, extract with dichloromethane and concentrate the extracts to a residue. Chromatograph the residue (silica gel, 5:95 ethyl acetate/dichloromethane) to give the title compound (230 mg), ms (FAB)=534 (M+1).

The following compounds can be prepared using a similar procedure:

N-[6,7-dimethoxy-3-(3,4-dimethoxyphenyl)-1,2,3,4-tetrahydroisoquinoline]-9-Z-octadecenamide, ms=594 (M+1); and N-[1-(2-methylamino-5-chlorophenyl)-1,2,3,4-tetrahydroisoquinnoline]-9-Z-octadecenamide, ms (FAB)=537 (M+1).

EXAMPLE 4

N-(1-benzyl-6,7-dihydroxy-1,2,3,4-tetrahydroisoquinoline)-9-Z-octadecenamide

Add 1(3'-dimethylaminopropyl)-3-ethylcarbodiimide hydrochloride (410 mg) to a mixture of 1-benzyl-6,7-dihydroxy-1,2,3,4-tetrahydroisoquinoline (500 mg), oleic acid (560 mg), 1-hydroxybenzotriazole (290 mg), N-methylmorpholine (220 mg) and dimethylformamide (8 mL), and stir for 18 h. Pour the mixture into water, extract with ethyl acetate, dry the combined extracts over Na₂SO₄, filter and concentrate the filtrate to a residue. Chromatograph the residue on silica gel (1:1 ethyl acetate/hexane) to give the title compound (460 mg), ms=520 (M+1).

The following formulations exemplify some of the

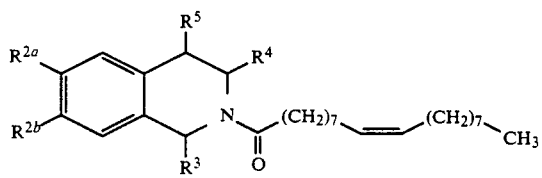

| Compound # | $R^3$ | $R^4$ | $R^5$ | $R^{2a}$ | $R^{2b}$ | Physical Data |
|---|---|---|---|---|---|---|
| 1A | H | H | H | H | H | ms = 397 (M⁺) |
| 1B | H | H | H | $CH_3O$ | $CH_3O$ | ms = 458 (M+1) |
| 1C | 4-Cl—C₆H₄—(CH₂)₂— | H | H | $CH_3$ | $CH_3O$ | ms = 580 (M+1) |
| 1D | 3,4-(CH₃O)₂C₆H₄—CH₂— | H | H | $CH_3O$ | $CH_3O$ | ms = 608 (M+1) |
| 1E | C₆H₅—CH₂— | H | H | H | H | ms = 488 (M+1) |
| 1F | C₆H₅—CH₂— | H | H | $CH_3O$ | $CH_3O$ | ms = 548 (M+1) |

EXAMPLE 2

N-(6,7-dimethoxy-4-phenyl-1,2,3,4-tetrahydroisoquinoline)-9-Z-octadecenamide

Add 350 mg of oleoyl chloride to a suspension of the methanesulfonate salt of 6,7-dimethoxy-4-phenyl-1,2,3,4-tetrahydroisoquinoline (350 mg) and triethylamine (435 mg) in diethyl ether at 0° C. and stir for 2.5 h. Dilute the mixture with ethyl acetate, filter and concentrate the filtrate to a residue. Chromatograph on silica gel (4:6 ethyl acetate/hexane) to give 480 mg of the title compound, ms=534 (M+1).

EXAMPLE 3

N-(6,7-dimethoxy-3-phenyl-1,2,3,4-tetrahydroisoquinoline)-9-Z-octadecenamide

Add a solution of 6,7-dimethoxy-3-phenyl-1,2,3,4-tetrahydro-isoquinoline (286 mg) in dichloromethane to a mixture of oleic acid (300 mg), 240 mg of dicyclohexylcarbodiimide (DCC), 5 mg of 4-dimethylaminopyridine (DMAP) and methylene chloride (5 mL) and stir for 22 h. Filter the mixture and concentrate to a residue. Chromatograph on silica gel (3:7 ethyl acetate/hexane) to give the title compound (346 mg), ms=534 (M+1).

dosage forms of this invention. In each the term "active compound" designates a compound of formula I or Ia, preferably N-(6,7-dimethoxy-4-phenyl-1,2,3,4-tetrahydroisoquinoline)-9-Z-octadecenamide. However, this compound may be replaced by an equally effective amount of other compounds of formula I or Ia.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B

Capsules

| No. | Ingredient | mg/tablet | mg/tablet |
|-----|------------|-----------|-----------|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

We claim:

1. A compound of the formula

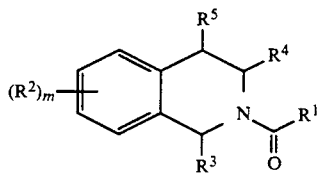

wherein $R^1$ is an alkyl chain of 10 to 25 carbons, branched or straight, saturated or containing 1-4 double bonds; an alkyl chain as defined substituted by 1-4 substituents selected from the group consisting of di-(lower alkyl)amino and Ar; an alkyl chain as defined interrupted by 1-4 groups selected from the group consisting of —O—, —SO$_p$—, —NH—, —C(O)—, phenylene, $R^2$-substituted phenylene, heteroarylene and $R^2$-substituted heteroarylene, wherein p=0, 1 or 2, and wherein heteroarylene is a divalent heteroaryl radical, wherein the heteroaryl is selected from the group consisting of pyridyl, pyrimidinyl, pyrazinyl, triazinyl, pyrrolyl, furanyl and thienyl, provided that where said alkyl chain is interrupted by 1-4 —NH— groups, said —NH— groups do not together with a —C(O)— group comprise an amide group; an interrupted alkyl chain as defined substituted by 1-4 di-(lower alkyl)amino or Ar groups; diphenylamino; di-($R^2$-substituted phenyl)amino; di-(heteroaryl)amino, wherein heteroaryl is as defined above; di-($R^2$-substituted heteroaryl)amino, wherein heteroaryl is as defined above; diphenylmethyl; or di-($R^2$-substituted phenyl)methyl;

$R^2$ is independently selected from the group consisting of hydroxy, lower alkyl, lower alkoxy, halogeno, amino, lower alkylamino and di-(lower alkyl)amino;

$R^3$, $R^4$ and $R^5$ are independently H or —(CH$_2$)$_n$—Ar;

Ar is selected from the group consisting of phenyl, $R^2$-substituted phenyl, heteroaryl and $R^2$-substituted heteroaryl, wherein heteroaryl is as defined above;

n=0, 1 or 2;

m=0, 1 or 2;

or a pharmaceutically acceptable salt thereof.

2. A compound of claim 1 wherein —C(O)—$R^1$ is selected from the group consisting of oleoyl, stearoyl, palmitoyl, linoleoyl, linolenoyl, elaidoyl, arachidonoyl, eicosapentaenoyl, eicosatetraenoyl, diphenylacetyl, 2,2-dimethylundecanoyl, 3-methoxy-4-(tetradecyloxy)-benzoyl, phenoxyundecanoyl and N,N-diphenylaminocarbonyl.

3. A compound of claim 2 wherein —C(O)—$R^1$ is oleoyl, diphenylacetyl or N,N-diphenylaminocarbonyl.

4. A compound of claim 1 wherein $R^2$ is hydroxy, methyl or lower alkoxy, and m=0, or 2.

5. A compound of claim 1 wherein one of $R^3$, $R^4$ or $R^5$ is —(CH$_2$)$_n$—Ar, wherein Ar is phenyl or $R^2$-substituted phenyl, and the others are H.

6. A compound of claim 1 wherein $R^3$, $R^4$ and $R^5$ are independently H or —(CH$_2$)$_n$—Ar, wherein Ar is phenyl or $R^2$-substituted phenyl.

7. A compound of claim 1 wherein $R^5$ is H or phenyl.

8. A compound of claim 7 wherein —C(O)—$R^1$ is oleoyl, diphenylacetyl or N,N-diphenylaminocarbonyl.

9. A compound of claim 1 wherein $R^4$ is H, phenyl or di-(lower alkoxy)phenyl.

10. A compound of claim 9 wherein $R^5$ is H or phenyl.

11. A compound of claim 10 wherein —C(O)—$R^1$ is oleoyl, diphenylacetyl or N,N-diphenylaminocarbonyl.

12. A compound of claim 1 wherein $R^3$ is selected from the group consisting of H, 2-(4-chlorophenyl)ethyl, 3,4-dimethoxyphenylmethyl, benzyl or 2-methylamino-5-chlorophenyl.

13. A compound of claim 12 wherein $R^5$ is H or phenyl.

14. A compound of claim 13 wherein —C(O)—$R^1$ is oleoyl, diphenylacetyl or N,N-diphenylaminocarbonyl.

15. A compound of claim 1 represented by the formula

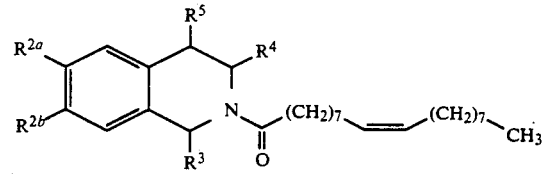

wherein

| Compound # | $R^3$ | $R^4$ | $R^5$ | $R^{2a}$ | $R^{2b}$ |
|---|---|---|---|---|---|
| 1A | H | H | H | H | H |
| 1B | H | H | H | CH$_3$O | CH$_3$O |
| 1C | 4-Cl—C$_6$H$_4$—(CH$_2$)$_2$— | H | H | CH$_3$ | CH$_3$O |
| 1D | 3,4-(CH$_3$O)$_2$—C$_6$H$_4$—CH$_2$— | H | H | CH$_3$O | CH$_3$O |
| 1E | C$_6$H$_5$—CH$_2$— | H | H | H | H |
| 1F | C$_6$H$_5$—CH$_2$— | H | H | CH$_3$O | CH$_3$O |
| 1 | C$_6$H$_5$ | H | H | CH$_3$O | CH$_3$O |
| 2 | H | H | C$_6$H$_5$ | CH$_3$O | CH$_3$O |
| 3 | H | C$_6$H$_5$ | H | CH$_3$O | CH$_3$O |
| 3A | H | 3,4-(CH$_3$O)$_2$—C$_6$H$_5$— | H | CH$_3$O | CH$_3$O |
| 3B | 2-NH$_2$-5-Cl—C$_6$H$_5$ | H | H | H | H |
| 4 | C$_6$H$_5$—CH2— | H | H | OH | OH |

16. A pharmaceutical composition useful for treating atherosclerosis in mammals comprising an ACAT-inhibitory effective amount of a compound of claim 1 in a pharmaceutically effective carrier.

* * * * *